United States Patent [19]

Mortensen

[11] Patent Number: 4,583,969
[45] Date of Patent: Apr. 22, 1986

[54] APPARATUS AND METHOD FOR IN VIVO EXTRAPULMONARY BLOOD GAS EXCHANGE

[76] Inventor: J. D. Mortensen, 10600 Dimple Dell Rd., Salt Lake City, Utah 84092

[21] Appl. No.: 624,627

[22] Filed: Jun. 26, 1984

[51] Int. Cl.$^4$ .............................................. A61M 3/00
[52] U.S. Cl. ....................................... 604/49; 604/4; 261/122; 623/1; 623/9; 623/12; 623/66
[58] Field of Search ...................... 261/DIG. 28, 122; 604/4, 48, 147, 23–26, 52–53; 128/DIG. 3, 632, 635; 3/1; 422/45

[56] References Cited

U.S. PATENT DOCUMENTS

| 3,505,686 | 4/1970 | Bodell | 3/1 |
|---|---|---|---|
| 3,794,468 | 2/1974 | Leonard | 23/258.5 |
| 3,856,475 | 12/1974 | Marx . | |
| 4,231,878 | 11/1980 | Esmond | 422/48 |
| 4,239,729 | 12/1980 | Hasegawa et al. | 422/48 |
| 4,265,249 | 5/1981 | Schnidler | 128/635 |
| 4,268,279 | 5/1981 | Shindo et al. | 55/16 |
| 4,306,018 | 12/1981 | Kirkpatrick | 435/2 |
| 4,374,802 | 2/1983 | Fukasawa | 422/48 |
| 4,376,095 | 3/1983 | Hasegawa | 422/46 |
| 4,387,711 | 6/1983 | Merry | 128/207.15 |

FOREIGN PATENT DOCUMENTS 1280481 11/1961 France ................................ 604/101

OTHER PUBLICATIONS

Bodell et al., "A Capillary Membrane Oxygenator," J. Thoracic and Cardiovas. Surg. 46:639 (1963).
Bodell, "An Implantable Artificial Lung," JAMA 191:125 (Jan. 25, 1965).
Galletti et al., "Development of an Implantable Booster Lung," Trans. ASAIO 24:573 (1980).
Tanishita et al., "Augmentation of Gas Transfer with Pulsatile Flow in the Coiled Tube Membrane Oxygenator Design," Trans. ASAIO 26:526 (1980).
Barthelemy et al., "Total Extracorpreal $CO_2$ Removal in a Pumpless Artery-To-Vein Shunt," Trans. ASAIO 28:354 (1982).
Kolobow et al., "Carbon Dioxide and the Membrane Artificial Lung: Their Roles in the Prevention and Treatment of Respiratory Failure," Trans. ASAIO 28:20 (1982).
Phillips, et al., "Percutaneous Initiation of Cardiopulmonary Bypass," Annals of Thoracic Surg. 36:223 (1983).

Primary Examiner—Stephen C. Pellegrino
Assistant Examiner—Gene B. Kartchner
Attorney, Agent, or Firm—Workman, Nydegger & Jensen

[57] ABSTRACT

A method and apparatus for the in vivo oxygenation of blood without using or disturbing the patient's lungs. The apparatus comprises a plurality of small diameter gas permeable tubes connected to headers at each end. The headers in turn are connected on one end to a source of oxygen rich gas and on the other end to an exhaust means. The apparatus is positioned within the circulatory system of a patient. Particularly, an incision is made in the patient's femoral or iliac vein and the apparatus is threaded through the vena cavae and eventually out an incision in the patient's jugular vein. Both headers are positioned so that a source of oxygen rich gas can be attached and the gas circulated through the device.

16 Claims, 5 Drawing Figures

APPARATUS AND METHOD FOR IN VIVO EXTRAPULMONARY BLOOD GAS EXCHANGE

BACKGROUND

1. Field of the Invention

The present invention relates to methods and apparatus for adding oxygen to and removing carbon dioxide from blood in vivo without involving the patient's lungs.

2. The Prior Art

Thousands of patients in hospitals each day are hypoexemic and/or have inadequate removal of carbon dioxide ($CO_2$) from their circulating blood. These conditions of inadequate blood gas exchange, which include both inadequate blood oxygenation and inadequate removal of $CO_2$, are commonly caused by varying degrees of respiratory inadequacy usually associated with acute lung illnesses such as pneumonitis, atelectasis, fluid in the lung or obstruction of pulmonary ventilation. Various heart and circulatory ailments such as heart disease and shock can adversely affect the flow of blood and thereby also reduce the rate of blood gas exchange.

Currently the most widely used methods of treating these types of blood gas exchange inadequacies involve increasing the flow of oxygen through the lungs by either increasing the oxygen concentration of the inspired gases or by mechanically ventilating the lungs. Both methods result in placing further pressure on the lungs, which may be diseased and unable to function at full capacity. In order to allow diseased or injured organs to heal it is generally best to allow those organs a period of rest followed by a gradual increase in activity. The current methods of treating inadequate blood gas exchange, however, force the diseased or damaged lungs to work even harder rather than allowing them a period of rest and recovery.

Various devices have been developed which are capable, at least for a limited period of time, of taking over the gas exchange function of the lungs. Many extracorporeal blood oxygenators are in common use and are employed most frequently during heart surgery. These devices are capable of providing blood oxygenation sufficient to carry the patient through the surgical procedure, at least when employed in conjunction with techniques, such as hypothermia, which reduce the body's demand for oxygen. These blood oxygenators include devices which bubble oxygen into the blood as the blood flows through the device. This is usually followed by a section of the device which defoams the blood to make it acceptable for reinjection into the patient.

Another group of extracorporeal oxygenators employ gas permeable membranes. These devices take many different shapes and configurations, however, the basic concept of operation is the same in all of these devices. Blood flows on one side of the gas permeable membranes while an oxygen rich gas flows on the other side of the membrane. As The blood flows through the device, the oxygen travels across the gas permeable membrane and enters the blood. This allows oxygenation of the blood without actually introducing oxygen bubbles into the blood and without the corresponding need for an extensive defoaming apparatus.

Neither of the types of oxygenators discussed above are particularly adaptable for use outside the setting of a cardiopulmonary bypass procedure, and are thus typically designed only for short term extracorporeal use. As a result, these devices are not of use in the day-to-day treatment of the typical patient suffering from lung disease or circulatory deficiency.

If oxygen could be added to and carbon dioxide removed from the circulating blood simply, effectively and harmlessly so as not to molest or irritate the sick or failing lungs, thus permitting the lungs to temporarily rest and recover without adversely effecting needed blood gas exchange, a significant and potentially very widely applicable breakthrough in hospital care would have been realized.

PRINCIPAL OBJECTS AND BRIEF SUMMARY OF THE INVENTION

In view of the foregoing, it is a primary object of the present invention to provide an apparatus and method for routine in vivo addition of oxgen to and removal of carbon dioxide from venous blood without involving the patient's lungs.

It is a further object of the present invention to provide in vivo blood oxygenation using a device which can be used on a temporary basis and which can be positioned and removed without the necessity of extensive surgical procedures.

It is also an object of the present invention to provide a device for in vivo blood oxygenation which is relatively nonthrombogenic but which is also efficient in the exchange of the various blood gases.

Another object of the present invention is to allow oxygen to be added to and carbon dioxide removed from the circulating blood simply, effectively and harmlessly without molesting, forcing, or irritating ailing lungs.

These and other objects and advantages of the present invention will become more fully apparent from the following description and appended claims taken in conjunction with the accompanying drawings.

In accordance with the foregoing objects, the present invention is directed to a novel apparatus and method for in vivo extrapulmonary oxygenation of blood. The apparatus and method of the present invention are designed for use on a routine basis and can be used without the necessity of major surgical procedures. Particularly, the present invention can be used instead of the routine lung ventilation now used to treat patients with inadequate blood gas exchange.

In one presently preferred embodiment, the apparatus of the present invention comprises a plurality of small diameter gas permeable tubes connected to headers at each end, and the headers in turn are connected on one end to a source of oxygen rich gas and on the other end to an exhaust tube or other means for allowing the gas to flow out of the device. The apparatus is inserted into a patient's vena cava. An incision is made in the patient's jugular vein and a radiopaque guide catheter is inserted and is guided through the superior and inferior venae cavae using a fluoro-scope, so as to exit through an incision in the common femoral or iliac vein. The apparatus is then attached to the quide catheter exiting from the femoral or iliac vein and is pulled into the vena cava by withdrawing the guide catheter from the jugular vein.

Once in place oxygen enriched gas is allowed to flow at relatively low pressure through the gas permeable tubes. Venous blood will flow around the small gas permeable tubes with oxygen passing from the tubes into the blood, causing blood oxygenation and carbon dioxide passing from the blood into the tubes and thence out of the body. The tubes are constructed of a material which allows oxygen and other gases to readily pass through their walls but which will not allow liquids, such as blood, to penetrate and which is also relatively nonthrombogenic.

DETAILED DESCRIPTION OF THE PREFERRED EMBODIMENTS

Figure 1:
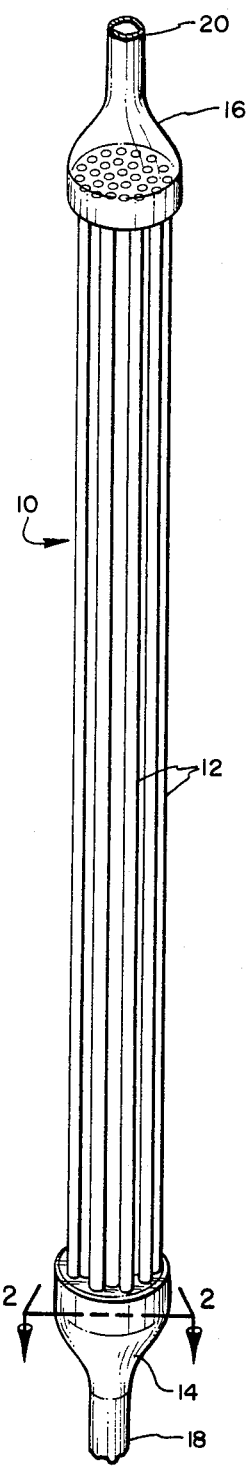
FIG. 1 is a perspective view of one preferred embodiment of the apparatus of the present invention.

Reference is next made to the drawings wherein like parts are designated with like numerals throughout. FIG. 1 represents one preferred embodiment of the apparatus of the present invention which is generally designated at 10. The apparatus comprises a plurality of small, thin-walled, gas permeable tubes 12. The small tubes 12 are connected at each end to a header. The header at the base of the device is indicated at 14 and the header at the top of the device is indicated at 16.

The gas permeable tubes 12 are designed and constructed so that molecules of oxygen and carbon dioxide are able to migrate across the tubing walls but at the same time the walls are impermeable to blood or other liquids and larger bubbles of gas. As discussed more thoroughly below, tubes 12 are also constructed of a relatively nonthrombogenic material. One currently favored material is a membrane of polyalkylsulfone (PAS) approximately 2.5 to 4 microns thick imbedded on a porous tubular framework constructed of a material such as ethyl cellulose. Another preferred construction for tubes 12 comprises a layer of silicone rubber approximately 25 microns thick placed on a similar porous tubular framework. In the event greater gas exchange across the membrane is desired, another alternative is to construct tubes 12 of a microporous membrane using a material such as polypropylene, polytetrafluorethylene, or polyethylene, although those materials are believed somewhat less biocompatible than the materials discussed above and may also allow the formation of undesirable microbubbles. Other factors which may influence material selection include freedom from pinholes, fragility, commercial availability and cost.

Figure 2:
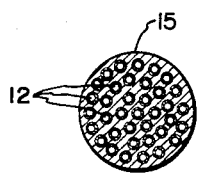
FIG. 2 is a cross-sectional view of the apparatus of FIG. 1 along line 2—2.

As shown best in the cross-sectional view of FIG. 2, the tubes 12 are preferably spaced from one another so that blood may flow through the apparatus and around the walls of each tube, thus enhancing blood gas exchange through the walls of each tube. The ends of tube 12 are firmly anchored in headers 14 and 16 by "potting" the tubes in a molded base 15 of silicon rubber or other biocompatible material. After the molded base 15 is cured, the end is cut away to leave the ends of tubes 12 unobstructed to gas flow. The headers 14 and 16 are then bonded around each base 15 to form a gas tight seal so that oxygen bubbles cannot escape into the patient's venae cavae once the apparatus has been inserted therein.

The configuration, length and diameter of the tubes 12 could vary according to the needs of each particular situation. However, it is the general goal in designing the device to maximize blood-membrane surface exposure and resultant oxygen-carbon dioxide transfer while minimizing the obstruction to normal blood flow. The currently preferred embodiment of the device includes about 30 tubes approximately 50 centimeters (cm) in length and 1 millimeter (mm) in outside diameter. The entire apparatus is about 1.5 cm in diameter in the case of an adult. Such a configuration would expose about 468 $cm^2$ of gas permeable area to the flowing blood.

The size and number of tubes used could vary from that described above in order to adapt the device to various other situations and applications. In one alternative embodiment (see FIG. 3) the apparatus would include about 500 tubes approximately 250 cm in length and about 0.25 mm in outside diameter. To accommodate the increase in tubing length without increasing the overall length of the apparatus, the tubes 32 are intertwined as described more fully below. This configuration would result in about 9,750 $cm^2$ of gas permeable surface area, which is an increase of more than 20 times the gas permeable surface area of the preferred embodiment discussed above.

Any number of other configurations could be used depending on the demands of the particular situation. It is currently anticipated that the tubes could vary in diameter from about 0.25 mm to about 1 mm and that they could vary in length from about 50 cm to about 250 cm. The number of tubes used could also vary from 30 or less up to 500 or more. As was mentioned above, the result is that the gas transfer surface area can be varied from about 468 $cm^2$ to almost 10,000 $cm^2$ depending on the specific requirements of the particular situation. Table 1 below summarizes some of the possible configurations of the apparatus including expected gas transfer rates.

TABLE 1

| Specifications for Gas Transfer Tubes | | | | Expected In Vivo Gas Transfer* | | | | | |
|---|---|---|---|---|---|---|---|---|---|
| | | | | 25 micron Silicone Rubber | | 4 micron PAS | | Microporous Polypropylene | |
| Outside Diameter | Length | Number of Tubes | Surface Area of Membrane Exposed to Blood | $O_2$ cc/min | $CO_2+$ cc/min | $O_2$ cc/min | $CO_2$ cc/min | $O_2$ cc/min | $CO_2$ cc/min |
| 1 mm | 50 cm | 30 | 468 $cm^2$ | 2.5 | 3.1 | 12.6 | 16.3 | 4.3 | 5.5 |
| 0.5 mm | 50 cm | 100 | 780 $cm^2$ | 4.2 | 5.1 | 21.0 | 24.6 | 7.2 | 9.2 |
| 0.25 mm | 50 cm | 500 | 1,950 $cm^2$ | 10.6 | 12.7 | 49.9 | 56.8 | 17.9 | 23.0 |
| 0.5 mm | 150 cm | 100 | 2,340 $cm^2$ | 12.7 | 15.2 | 59.8 | 68.2 | 21.5 | 27.6 |
| 0.25 mm | 150 cm | 500 | 5,850 $cm^2$ | 31.8 | 38.1 | 149.7 | 170.4 | 53.8 | 69.0 |

TABLE 1-continued

| Specifications for Gas Transfer Tubes | | | | Expected In Vivo Gas Transfer* | | | | | |
|---|---|---|---|---|---|---|---|---|---|
| | | | | 25 micron Silicone Rubber | | 4 micron PAS | | Microporous Polypropylene | |
| Outside Diameter | Length | Number of Tubes | Surface Area of Membrane Exposed to Blood | $O_2$ cc/min | $CO_2+$ cc/min | $O_2$ cc/min | $CO_2$ cc/min | $O_2$ cc/min | $CO_2$ cc/min |
| 0.25 mm | 250 cm | 500 | 9,750 cm$^2$ | 53.0 | 63.5 | 249.5 | 284.0 | 89.7 | 115.1 |

*Based on reported gas transfer experience with these specific membranes when applied to venous blood under clinically relevent blood flow rate, blood gas, temperature, and hemoglobin content conditions.
**This figure varies markedly, depending on gas flow rate through the gas transfer tubes. Figures included in this table are the lowest estimated $CO_2$ transfer. By increasing the gas flow rate, this could be increased 2 to 4 fold.

Figure 3:
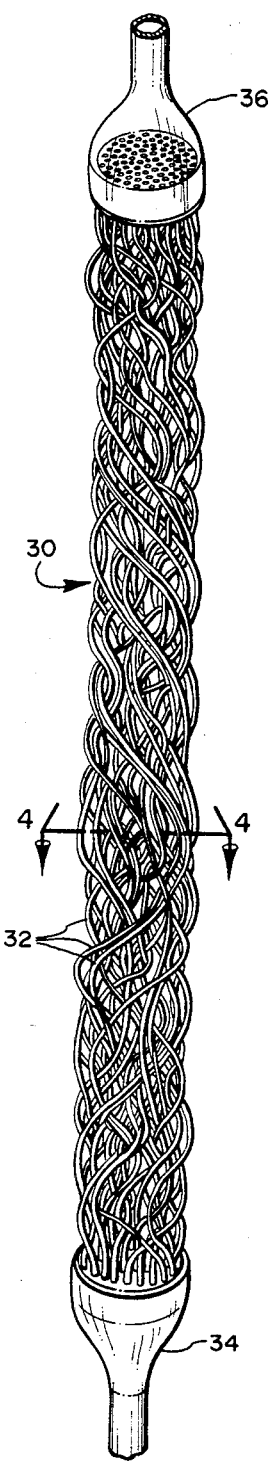
FIG. 3 is a perspective view of an alternative preferred embodiment of the device of the present invention.

In the event that it is found to be desirable to use very long tubes it may be necessary to intertwine them so that they will still fit within a patient's vena cava. FIG. 3 illustrates an apparatus using such a configuration. The apparatus is generally designated 30. As in the first embodiment discussed above, this embodiment has a plurality of tubes 32 which are potted at the ends thereof and attached to headers. The header at the top of the device is designated 36 and the header at the base of the device is designated 34. With the exception of the spiral configuration of the tubes 32, the apparatus illustrated in FIG. 3 is similar to the device illustrated in FIG. 1. It is anticipated, for example, that both devices would use the same gas permeable materials for tubes 12 or 32 and both devices could use similar headers.

Figure 4:
FIG. 4 is a cross-sectional view of the apparatus of FIG. 3 along line 4—4.

FIG. 4 is a cross-sectional view of the embodiment of the device shown in FIG. 3. Sufficient space is provided between each of the tubes 32 to permit blood to flow freely between and around the tubes.

Figure 5:
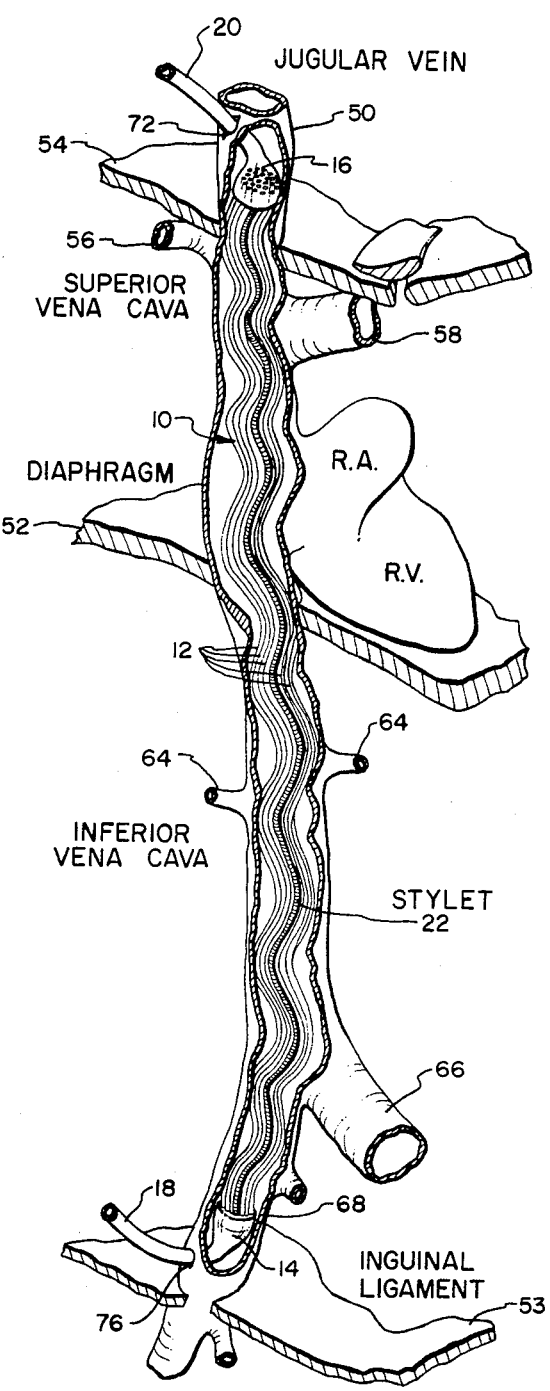
FIG. 5 is a perspective view of the device illustrated in FIG. 1 positioned within a patient's venae cavae, with a portion of the venae cavae broken away.

Reference is next made to FIG. 5 wherein the method of using the present invention is illustrated. The superior vena cava and the inferior vena cava are labeled in FIG. 5. Also labeled are the jugular vein 50, the diaphragm 52, the right ventricle of the heart (designated R.V.) the right atrium (designated R.A.) and the inguinal ligament 53. Also illustrated in FIG. 3 are the patient's clavicle 54, the right subclavian vein 56, the innominate vein 58, the renal veins 64, the left common iliac vein 66, and the right external iliac vein 68.

As can be seen in FIG. 5 the apparatus 10 is inserted through an incision 76 into the right external iliac or right femoral vein 68. The apparatus is threaded or pulled through the superior and inferior venae cavae by known means such as through the use of a radiopaque catheter and a fluoroscope (not shown), as discussed briefly above. The tubing 18 connected to header 14 will then enter the patient through incision 76 in the right external iliac or common femoral vein. The tubing 20 will then exit the patient through incision 72 in the right jugular vein 50.

While the apparatus 10 is in place header 14 will be connected to a source of oxygen enriched gas through tubing 18 and header 16 will be connected to an exhaust means through tubing 20. As a result, the oxygen enriched gas will travel through header 14 into tubes 12 and upwardly until it reaches header 16 and travels out of the device. During the time the gas is within tubes 12 it will be able to permeate the tubes 12 and oxygenate the blood traveling through the venae cavae. In addition, carbon dioxide will be able to leave the blood and flow into tubes 12 and thereby be exhausted from the system. As discussed above, while oxygen and carbon dioxide can readily travel through the walls of tubes 12, blood cannot enter the tubes. As a result, oxygenation can occur without the blood being directly exposed to gas bubbles.

It is presently anticipated that the gas entering tubes 12 may be 100% oxygen flowing at a rate of about 0.6 to 1.2 liters/minute. This will allow the device to operate at relatively low pressures within the range of 5–10 millimeters of mercury (mmHg). Operation of the device at relatively low pressures will provide adequate blood oxygenation without a substantial risk of creating leaks or bubbles within the venae cavae. In addition, it may be desirable to apply controlled suction to the gas leaving tubes 12 through header 16 in order to increase the flow of gas without unduly increasing pressures.

In order to assure adequate contact between the blood and the device and to avoid laminar blood flow and the formation of a boundary layer along the device, it may be desirable to place the device in a "wavy", undulating, or spiral configuration. FIG. 5 illustrates the device in such a configuration. Such a pattern may be achieved by various means, however, one possible means would be to include a rigid or semi-rigid stylet 22 which runs parallel to the tubes 12 and which is securely attached to headers 14 and 16. Stylet 22 may be formed of blood-compatible metal or plastic so that it may be bent to the desired configuration before inserting the device into the patient, thereby assuring that the apparatus will maintain an undulating or spiral configuration once in place.

In employing a device such as the device of the present invention it is critical to minimize thrombosis formation. Failure to adequately deal with this problem has been a factor in defeating prior attempts to artificially oxygenate blood. This problem may be dealt with by constructing the device using nonthrombogenic materials. In the event that thrombosis formation is still a problem it may be possible to coat the surface of the tubes 12 with an additional thrombo-resistant material or to treat the patient with platelet-sparing medications.

The present device is a vast improvement over prior attempts to artificially oxygenate blood. The present device, unlike routine treatments for lung diseases, allows the lungs to rest and recover from their ailment. It is also possible to use the present device for routine, temporary treatment. Prior blood oxygenators are principally used only during surgical procedures and are placed outside the body. In addition, the present device uses as its outer wall the venae cavae insitu. Blood is not flowed through artificial tubing or other devices. As a result, damage to the blood, including hemolysis and thrombosis formation, is minimized. Thus, the present invention provides for the efficient and relatively nontraumatic in vivo oxygenation of blood without involving the ailing lungs.

It will be appreciated that the apparatus and method of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for effecting in vivo extrapulmonary blood gas exchange comprising the steps of:
   attaching a plurality of gas permeable tubes to a first header at the inlet end of said tubes and to a second header at the outlet end of said tubes;
   positioning said gas permeable tubes within the venae cavae of a patient;
   connecting said first header to a source of oxygen enriched gas;
   connecting said second header to a means for exhausting gas carried by said tubes;
   passing said oxygen enriched gas through said gas permeable tubes at a rate of from 0.6 to 1.2 liters per minute and at a pressure of from 5 to 10 mm Hg such that blood flowing through said venae cavae is oxygenated as carbon dioxide is removed from said blood into said gas permeable tubes; and
   applying controlled suction to said second header.

2. A method as defined in claim 1 wherein said step of positioning said gas permeable tubes within said venae cavae comprises the steps of:
   preparing a first incision in said patient's right jugular vein and a second incision at one of the right external iliac or common femoral veins of said patient;
   inserting a guide catheter into said patient's vena cava through said first incision;
   attaching said second header to said guide catheter and pulling said second header through said first incision into said vena cava to the point of said second incision; and
   attaching a first length of tubing to said second header and a second length of tubing to said first header.

3. A method as defined in claim 1 wherein said step of positioning said gas permeable tubes within said venae cavae comprises the steps of:
   attaching a semi-rigid stylet between said headers; and
   bending said stylet to form an undulating pattern followed by said tubes.

4. An apparatus for effecting in vivo extrapulmonary blood gas exchange comprising:
   a plurality of gas permeable tubes adapted for insertion into the venae cavae of a patient, said gas permeable tubes allowing for the passage of oxygen from said gas permeable tubes into blood flowing through said vena cavae and allowing for the passage of carbon dioxide from said blood into said gas permeable tubes, each said gas permeable tube having an inlet end adapted for placement in the inferior vena cava of the patient and an outlet end adapted for placement in the superior vena cava of the patient;
   a first header adapted for placement in the inferior vena cava and attached to the inlet ends of said gas permeable tubes, said first header having a molded base member into which the inlet ends of said gas permeable tubes are secured in spaced relation to one another;
   a second header adapted for placement in the superior vena cava and attached to the outlet ends of said gas permeable tubes, said second header having a molded base member into which the outlet ends of said gas permeable tubes are secured in spaced relation to one another;
   an oxygen inlet tube having one end thereof connected to said first header and the other end thereof in gaseous communication with a source of oxygen, said oxygen inlet tube being adapted for insertion through an incision formed in the inferior vena cava;
   a gas outlet tube having one end thereof connected to said second header, said gas outlet tube being adapted for insertion through an incision formed in the superior vena cava so as to provide exhaust means for said gas permeable tubes; and
   a semi-rigid stylet interconnecting said first and second headers so as to be positioned therebetween within said venae cavae, said style being bent so as to form an undulating pattern within said venae cavae to thereby minimize laminar blood flow around said gas permeable tubes within said venae cavae.

5. An apparatus as defined in claim 4 wherein the number of said tubes attached to said headers is from 30 to 500.

6. An apparatus as defined in claim 4 wherein each said tube comprises a membrane of polyakylsulfone of from 2.5 to 4 microns thick imbedded on a porous tubular framework constructed of ethyl cellulose.

7. An apparatus as defined in claim 4 wherein each said tube comprises a membrane of silicone rubber 25 microns thick imbedded on a porous tubular framework of ethyl cellulose.

8. An apparatus as defined in claim 4 wherein each tube comprises a microporous membrane of polypropylene.

9. An apparatus as defined in claim 4 wherein each tube comprises a microporous membrane of polypropylene.

10. An apparatus as defined in claim 4 wherein each tube comprises a microporous membrane of polytetrafluorethylene.

11. An apparatus as defined in claim 4 wherein each tube comprises a microporous membrane of polyethylene.

12. An apparatus as defined in claim 4 wherein said tubes are intertwined one with another along their length between said first and second headers.

13. An apparatus as defined in claim 4 wherein said tubes are from 50 cm to 250 cm in length, and from 0.25 mm to 1 mm in outside diameter.

14. A method for effecting in vivo extrapulmonary blood gas exchange comprising the steps of:
   attaching a plurality of gas permeable tubes to a first header at the inlet ends of said gas permeable tubes by securing said inlet ends in a molded base member formed in said first header so as to position said inlet ends in spaced apart relationship;
   attaching the outlet ends of said gas permeable tubes to a second header by putting said outlet ends into a molded base member formed in said second header so as to position said outlet ends in spaced apart relationship;

making a first incision in one of the right external iliac or common femoral veins of a patient and a second incision in the right jugular vein of said patient;

inserting a guide catheter into said patient's inferior vena cava through said first incision;

attaching said second header to said guide catheter and pulling said second header through said first incision and through said inferior vena cava to the point of said second incision so as to position said second header in said patient's superior vena cava and so as to position said first header in said patient's inferior vena cava, thereby positioning said gas permeable tubes within said venae cavae;

attaching a first length of tubing to said first header and a second length of tubing to said second header, said first length of tubing extending through said first incision and into the inferior vena cava and said second length of tubing extending through said second incision and into the superior vena cava;

connecting said first length of tubing to a source of oxygen enriched gas;

connecting said second length of tubing to a means for exhausting gas carried by said gas permeable tubes;

passing said oxygen enriched gas through said gas permeable tubes so as to provide for the passage of oxygen from said gas permeable tubes into blood flowing through said vena cavae and so as to allow for the passage of carbon dioxide from said blood into said gas permeable tubes; and minimizing laminar blood flow around said gas permeable tubes within said venae cavae by forming a semi-rigid stylet into an undulating configuration and positioning said stylet within said venae cavae between said first and second headers.

15. A method for effecting in vivo extrapulmonary blood gas exchange comprising the steps of:

securing a plurality of gas permeable tubes to a first header at the inlet ends of said tubes and to a second header at the outlet ends of said tubes such that said inlet and outlet ends are spaced one from the other to permit blood flow around and through the tubes held by each said header;

positioning said tubes and headers within the venae cavae of a patient;

forming a semi-rigid stylet into an undulating configuration and positioning said stylet within said venae cavae between said first and second headers to minimize laminar blood flow around said tubes;

connecting said first header to a source of oxygen enriched gas and connecting said second header to a means for exhausting gas carried by said tubes; and passing said oxygen enriched gas through said tubes such that blood flowing through said vena cavae is oxygenated as carbon dioxide is removed from said blood.

16. A method as defined in claim 15 wherein said step of positioning said gas permeable tubes within said venae cavae comprises the steps of:

preparing a first incision in said patient's right jugular vein and a second incision at one of the right external iliac or common femoral veins of said patient;

inserting a guide catheter into said patient's venae cavae through said first incision;

attaching said second header to said guide catheter and pulling said second header through said first incision into said venae cavae to the point of said second incision; and attaching a first length of tubing to said second header and a second length of tubing to said first header.

* * * * *

UNITED STATES PATENT AND TRADEMARK OFFICE
CERTIFICATE OF CORRECTION

PATENT NO. : 4,583,969
DATED : April 22, 1986
INVENTOR(S) : J. D. Mortensen

It is certified that error appears in the above-identified patent and that said Letters Patent is hereby corrected as shown below:

Column 1, line 60, "As The" should be --As the--
Column 2, line 9, "effecting" should be --affecting--
Column 2, line 59, "fluoro-scope" should be --fluoroscope--
Columns 5-6, last line of writing under table, "2 to 4 fold" should be --twofold to fourfold--
Column 6, line 57, "insitu" should be --in situ--
Column 8, line 31, "polyakylsulfone" should be --polyalkylsulfone--

Signed and Sealed this

Fifth Day of August 1986

[SEAL]

Attest:

DONALD J. QUIGG

Attesting Officer

Commissioner of Patents and Trademarks